United States Patent [19]

Jewett et al.

[11] 4,150,670
[45] Apr. 24, 1979

[54] ANESTHESIA DETECTOR AND DISPLAY APPARATUS

[75] Inventors: Warren R. Jewett; John B. Theiss; Lawrence Adler, all of Tucson, Ariz.

[73] Assignee: University Patents, Inc., Norwalk, Conn.

[21] Appl. No.: 851,141

[22] Filed: Nov. 14, 1977

[51] Int. Cl.² .................................................. A61M 16/00
[52] U.S. Cl. ..................................... 128/188; 128/210; 137/93; 73/23
[58] Field of Search ....... 128/188, DIG. 17, DIG. 29, 128/2 C, 2 E, 209, 210, 145.8; 137/93, 88; 73/23, 27 R

[56] References Cited

U.S. PATENT DOCUMENTS

| | | | |
|---|---|---|---|
| 3,465,753 | 9/1969 | Levy et al. ............................. | 128/188 |
| 3,536,088 | 10/1970 | Moyat ............................... | 128/188 X |
| 3,566,865 | 3/1971 | Hay ...................................... | 128/188 |
| 3,824,168 | 7/1974 | Oswin et al. ..................... | 128/2 C X |

Primary Examiner—Henry J. Recla
Attorney, Agent, or Firm—Merriam, Marshall & Bicknell

[57] ABSTRACT

An electromechanical monitor for rapid quantitative detection of an anesthetic gas in the gaseous flow of an anesthesia administration system wherein deformation due to directly proportional reversible swelling of an elastic membrane in contact with the gas is mechanically detected and translated into an electrical signal. The membrane is preferably disc-shaped, constructed of silicone rubber, and horizontally mounted within the device. The electrical signal developed may be employed to generate an information display and/or provide automatic control of anesthetic and other gas content within the system.

11 Claims, 9 Drawing Figures

ANESTHESIA DETECTOR AND DISPLAY APPARATUS

BACKGROUND OF THE INVENTION

The present invention relates generally to gas monitoring and control systems and more particularly to devices useful in quantitatively detecting narcotic gases or vapors within systems for administration of anesthetic gases to surgical patients.

Present anesthesia techniques provide for administration of controlled amounts of oxygen and one or more narcotic gases such as nitrous oxide or halogenated hydrocarbons. Halogenated materials commonly employed include, e.g., 1-bromo-1-chloro-2-2-2-trifluoroethane; 1,1,1-trifluoro-2-chloro-2-bromoethane (halothane); 1-bromo-1-chloro-2,2-difluoropropane; 2,2-dichloro-1,1-difluoroethylmethyl-ether. Administration of these materials in gaseous form is attended by numerous difficulties, including the delivery of exact quantities of anesthetic for inhalation by the patient, disposal of excess quantities exhaled by the patient, and/or recovery and re-use of exhaled gas. It is noteworthy, for example, that more precise knowledge of the quantities of anesthetic gases actually taken up by a patient during a surgical procedure can provide useful information concerning the physiological state of the patient (e.g., increases or decreases in cardiac output) as well as the structural integrity of the delivery system. Integrity of delivery systems and maintenance of a pollution-free atmosphere in operating rooms has become a more prominent concern as a result of recent evidence of possible carcinogenic activity of some anesthetic gases.

Proposed solutions to the problem of direct quantification of anesthetic gas within delivery systems have included both electromechanical and electromechanical-optical apparatus. U.S. Pat. No. 3,465,753, for example, relates to gas analysers wherein anesthetic concentration in a given volume of fluid is detected through fluorometric techniques. U.S. Pat. Nos. 3,498,309 and 3,536,088 relate to devices wherein length fluctuations generated by reversible swelling of elastic (e.g., silicone rubber) strips under constant tension and in contact with the narcotic gas delivered to a patient is translated into motion of a mechanical indicating member or actuation of optical means for generating an electrical signal.

While the above-mentioned prior art systems purport to accurately and reproduceably provide quantitative information, their use has revealed substantial functional inadequacies.

Fluorometric systems such as disclosed in the U.S. Pat. No. 3,465,753, for example, are notoriously inaccurate due to the inherent inadequacy of gas sampling schemes wherein only a small quantity of the gas to be analyzed is sampled. Further, fluorometric analysis ordinarily employs rather expensive and intricate light generating and sensing apparatus which provides temporally discontinuous, and therefore marginally useful, information concerning gas concentration.

Devices employing elastic strips as in the U.S. Pat. No. 3,498,309 and 3,536,088 are known to be especially susceptible to variations in temperature, water vapor content of the gas sampled, and mechanical vibration brought about by pressure changes in gas flow. In practice, their use has been essentially limited to monitoring input of anesthetic gas in gaseous flow delivered to a patient rather than anesthetic gas exhaled by the patient. Information so generated provides the anesthesiologist with substantially less than complete knowledge of the ongoing dynamics of the anesthesization process. When nitrous oxide and halothane mixtures are employed, for example, knowledge of halothane input concentration alone provides no information concerning the dynamic operation of "the second gas effect" upon the patient.

Other disadvantages of prior art apparatus measuring length variations in elastic strips include the difficulty in re-use, repair and replacement of components. It is noteworthy, for example, that while the devices of the U.S. Pat. Nos. 3,498,309 and 3,536,088 admit replacement of the silicone rubber strip elements, difficult manipulations are involved owing to the need to releasably secure both ends of the multiple strips with hooks or other similar fixing means. Because gas quantities are ascertained as a function of strip length changes, great care must be exercised in securing proper tension on the strips. Length-change-sensing means provided on the devices also dictate an interrelationship of elements rendering sterilization of the entire device prior to re-use impossible.

There has developed, therefore, a substantial need for gas anesthetic monitoring devices of relatively simple construction which would provide for generation of temporally continuous information concerning precise quantities of anesthetic gas in either patient input or output portions of the system. Ideal devices would be minimally sensitive to fluctuations in temperature, pressure and water vapor concentration, would be easily sterilizable and would incorporate component parts that are easily replaceable.

BRIEF SUMMARY

The present invention provides electromechanical devices for quantitative detection of anesthetic gas within a gaseous flow administration system. A preferred embodiment of the device incorporates, inter alia, a lower housing or cartridge having a gas inlet and outlet. Releasably secured within the housing—in a generally horizontal position—is a membrane of silicone rubber or other suitable elastic material which is supported about its entire periphery. Associated in a sealed relation with the lower housing is an upper housing supporting a linear variable differential transformer, a vertically-extending operative stem or armature of which is in contact with the surface of the elastic membrane. Relative pressure differentials above and below the membrane are avoided by allowing for essentially open communication between upper and lower housings.

In use, the detection apparatus is incorporated in either the input or output portions of an anesthetic delivery system and provides an electrical signal in response to deformation of the membrane resulting from the membrane's reversible swelling in direct proportion to the quantity of anesthetic gas continuously passing through the device. Suitable means are provided for calibration of the deformation-sensing, signal-generating apparatus to fixed quantities or proportions of anesthetic gas. Means may also be provided for additional calibration of the sensing apparatus in response to variations in ambient temperature.

Devices constructed according to the invention allow for extreme ease of replacement of the elastic membrane and sterilization of all appropriate parts prior to re-use. Preferred embodiments may include means for diminishing the potential adverse effects on membrane deformation due to high concentrations of water vapor in the administrative system, especially at or above the upper side of the membrane. Also contemplated are bacterial filtering means for avoiding contamination of electrical components of the upper housing without loss of desired pressure equalization.

The electrical signal developed by the devices may be employed to generate informational displays and permanent recordings for consideration by the anesthesiologist or may provide automatic control of gas flow of all types within the entire anesthesia administration system.

Other and further aspects and advantages of the invention will become apparent upon consideration of the following detailed description and the accompanying drawing, wherein:

DETAILED DESCRIPTION

Figure 1:
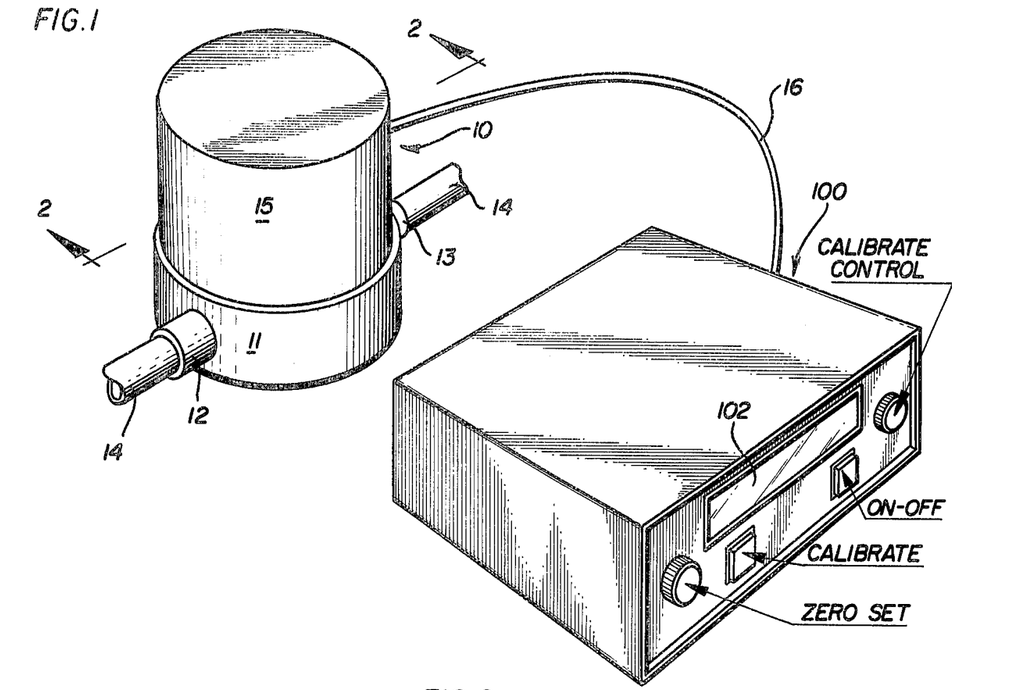
FIG. 1 illustrates detection apparatus of the invention in combination with informational display apparatus.

FIG. 1 illustrates an anesthetic monitoring system according to the invention wherein electromechanical detector 10 is shown in operative association with a console 100 incorporating electrical control and signal display apparatus. In this embodiment, detector 10 includes a lower cartridge or housing 11 having inlet member 12 and outlet member 13 for attachment of gaseous flow conduit elements 14, 14 of an anesthetic administration system (see, e.g., FIG. 6). Mounted atop housing 11 is upper housing 15 incorporating electromechanical sensing means electrically connected to console 100 by conduit 16.

Figure 7:
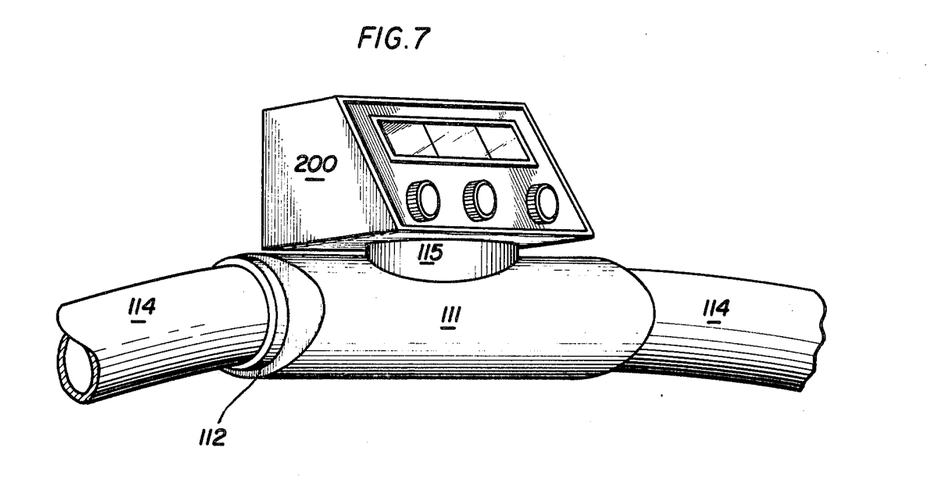
FIG. 7 illustrates an alternative embodiment of a detection apparatus of the invention.

An alternative association of anesthetic monitoring system components is shown in FIG. 7 wherein electrical control and signal display apparatus 200 is mounted atop lower cartridge or housing 111 and upper housing 115. As in FIG. 1, the lower housing is provided with inlet member 112 and outlet member (not shown), for attachment to gaseous flow conduit elements 114, 114 and the upper housing mounts an electromechanical sensing means. This association of components eliminates the need for exposed electrical conduits.

FIGS. 2, 3, 4, 8 and 9 illustrate preferred embodiments of a detector apparatus 10 in greater detail.

Figure 2:
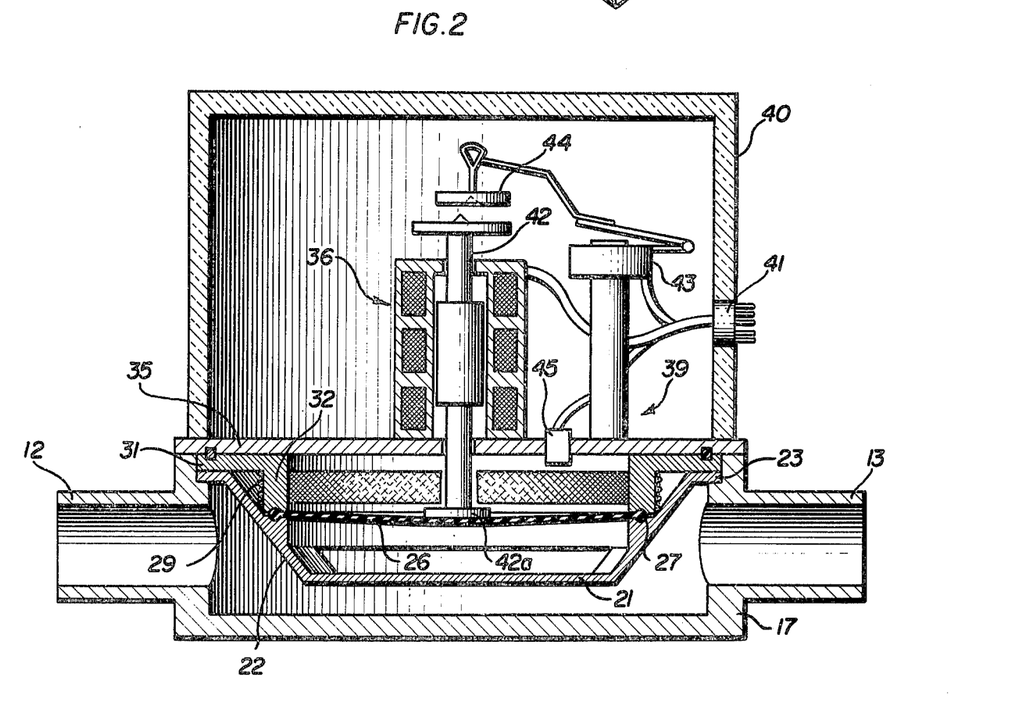
FIG. 2 is a cross-sectional view of the detection apparatus taken along line 2—2 of FIG. 1.
Figure 3:
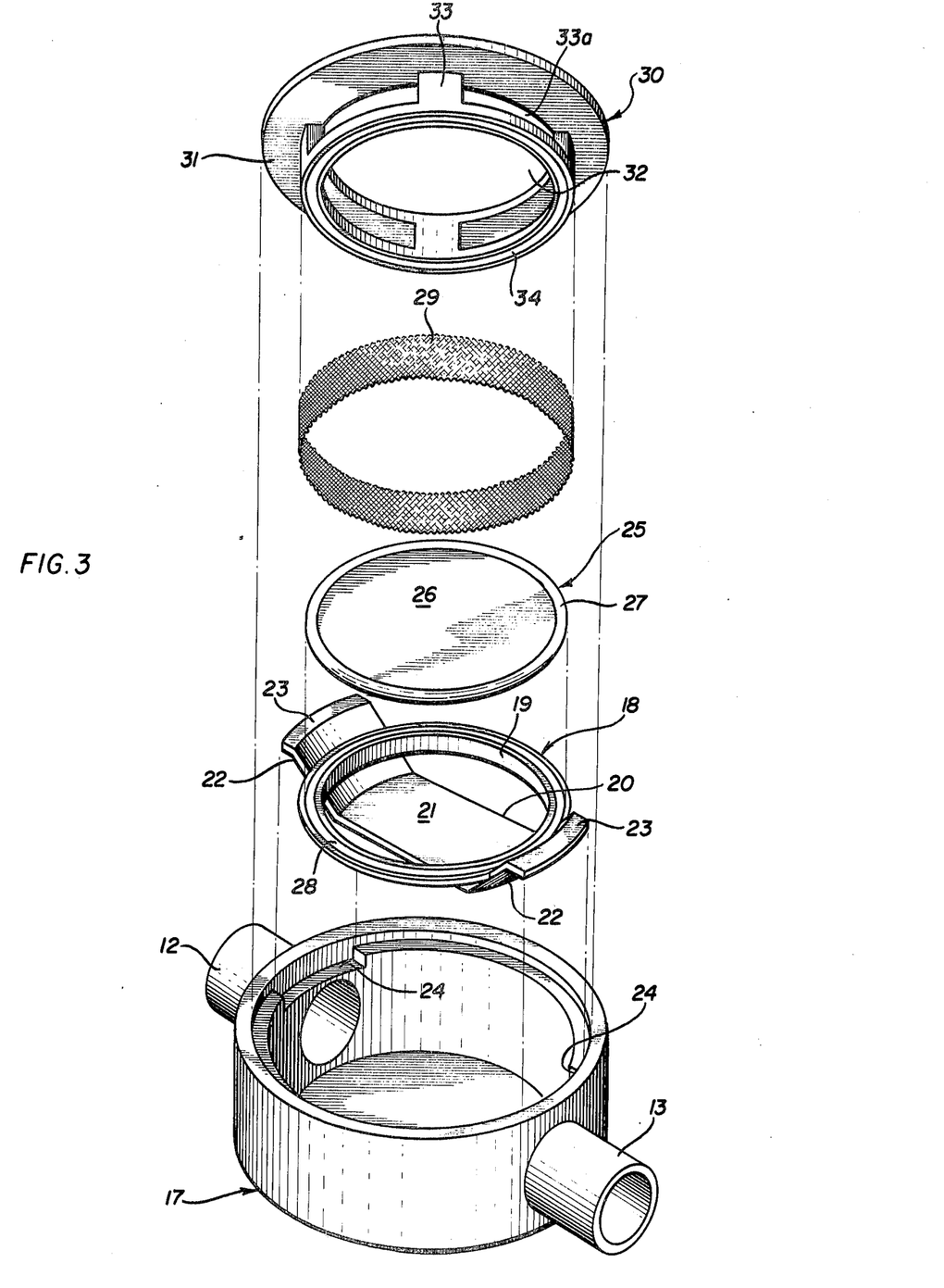
FIG. 3 is a partial exploded view of an elastic membrane-supporting, lower housing of the invention.

FIG. 2 illustrates assembled upper and lower housings and in FIG. 3 the elements of lower cartridge or housing 11 are shown in exploded view. (Unless otherwise indicated, all housing elements may be fabricated by injection molding of a polymeric material such as polycarbonate, high density polyethylene or other semi-rigid thermoplastic substance impervious to halogenated hydrocarbons.)

Housing 11 includes open drum member 17 provided with hollow, preferably tubular, inlet and outlet members, 12 and 13 respectively, for communication of the drum interior with gaseous flow through an anesthetic administration system. Diaphragm supporting member 18 consists of a ring element 19 having an outer diameter less than the inner diameter of drum 17. Affixed to ring 19 is gas flow baffle 20 having a base 21 and opposed upwardly and outwardly tapering sidewalls 22, 22. Each sidewall 22 is provided with an outwardly extending flange 23 dimensioned to be releasably fitted within a corresponding recess or slot 24 provided on the interior of drum 17.

The diaphragm/membrane element 25 consists of elastic material sheet 26 substantially supported by hoop element 27. Elastic sheet 26 may be fabricated of any suitable elastomeric substance which exhibits the property of reversible swelling in proportion to narcotic gas concentration. Suitable anesthetic gas-sensitive substances may include numerous polymers such as polyurethane or copolymers of butadiene and acrylonitrile. Preferred substances include silicone elastomers which may be injection molded in appropriate shapes (e.g., circular, rectangular, square) and thicknesses (from about 0.001 to 0.010 inches, and preferably about 0.005 inches). Hoop element 27 may be of unitary construction with sheet 26 or of metallic or rigid polymeric construction and is sized to allow releasable fitting into an annular recess 28 provided on ring 19 of diaphragm supporting member 18 so as to substantially horizontally and vertically align the membrane 25 in housing 11.

Silicone rubber diaphragm or membrane elements employed according to the invention exhibit an exceptionally small degree of sensitivity (i.e., variation in proportioned deformation) to fluctuations in water vapor content of the anesthetic gas flow monitored. To the extent that it may be desirable to further minimize sensitivity to water vapor and condensation above the diaphragm, moisture condensing and bacteria filtering screen member 29 in the form of an annular band fabricated from suitable plastic mesh can be provided to effectively insulate the top diaphragm 25 from direct contact with moisture and bacteria-laden air by condensing moisture into droplets which may fall downwardly and collect at the bottom of drum 17.

Diaphragm holder 18, diaphragm 25 and screen 29 are secured in place within drum 17 by housing cover element 30. Cover 30 includes a flat, annular portion 31 surrounding opening 32. Extending outwardly (and operatively downwardly) from annular portion 31 is a vented tubular flange 33 provided with an annular groove 34 (dimensionally similar to groove 19) for releasably securing membrane 25 in place within housing 11. In this embodiment the screen member 29 fits around flange 33 to filter vapor passing from lower housing 11 to upper housing 15 through vents 33a in flange 33. Housing cover 30 may be sized to be pressure fit atop drum 17 or may be attached by any suitable fastening means.

Figure 8:
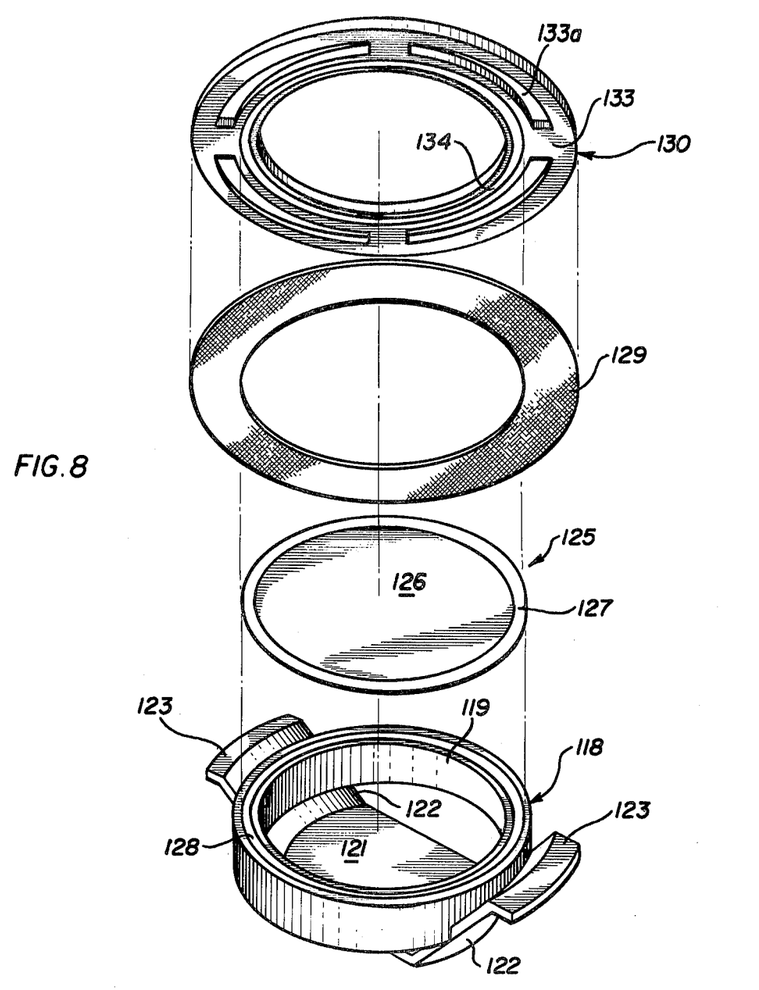
FIG. 8 illustrates an exploded view of an alternative configuration of certain membrane-supporting, lower housing elements of the invention.
Figure 9:
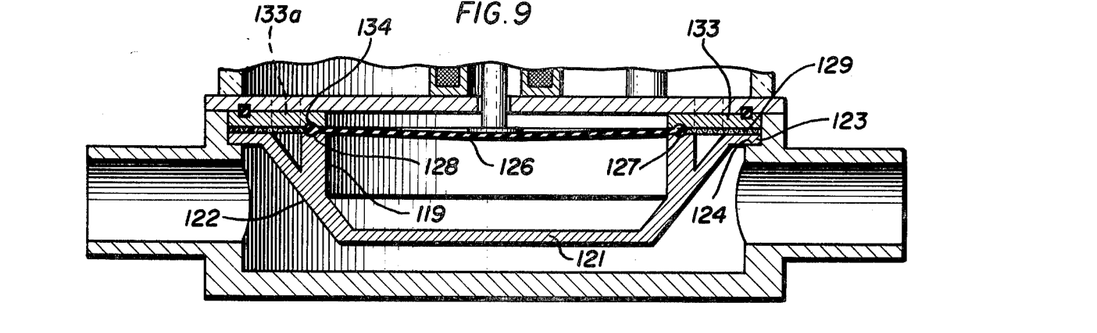
FIG. 9 is a fragmentary cross-sectional view of detection apparatus incorporating the elements shown in FIG. 8.

FIGS. 8 and 9 illustrate an alternative embodiment of lower housing parts according to the invention wherein there is again provided an open drum 117 with inlet and outlet members to accommodate gas flow. Diaphragm supporting member 118 consists of tubular ring element 119 having a diameter less than that of drum 117. Affixed to ring 119 is gas flow baffle 120 having a base 121 and opposed upwardly and outwardly tapering sidewalls 122, 122. As in the embodiment of FIGS. 2 and 3, each sidewall has a flange 123 for releasable fitting in a recess 124 of drum 117.

Diaphragm element 125 consists of sheet 126 supported by hoop element 127 which releasably fits in annular groove 128 of ring 119 as well as in groove 134 of substantially flat cover element 130. Bacterial and moisture screen 129 may be fashioned as a die-cut annulus disposed beneath openings 133a formed in cover element 130. Once again, screen 129 functions to filter out moisture and bacteria during pressure-equalizing gaseous flow from lower to upper housings.

The foregoing description reveals the lower housing of the device as comprising an inexpensively-fabricated, easily assembled and disassembled cartridge, supporting an anesthetic gas-sensitive membrane. A new cartridge may be employed for each new patient without encountering substantial expense. Alternately, the cartridge may be autoclaved and re-used repeatedly with occasional replacement of the moisture and bacterial screen. When the bacterial screen is employed there is no need to replace or autoclave the upper housing after each use.

Figure 4:
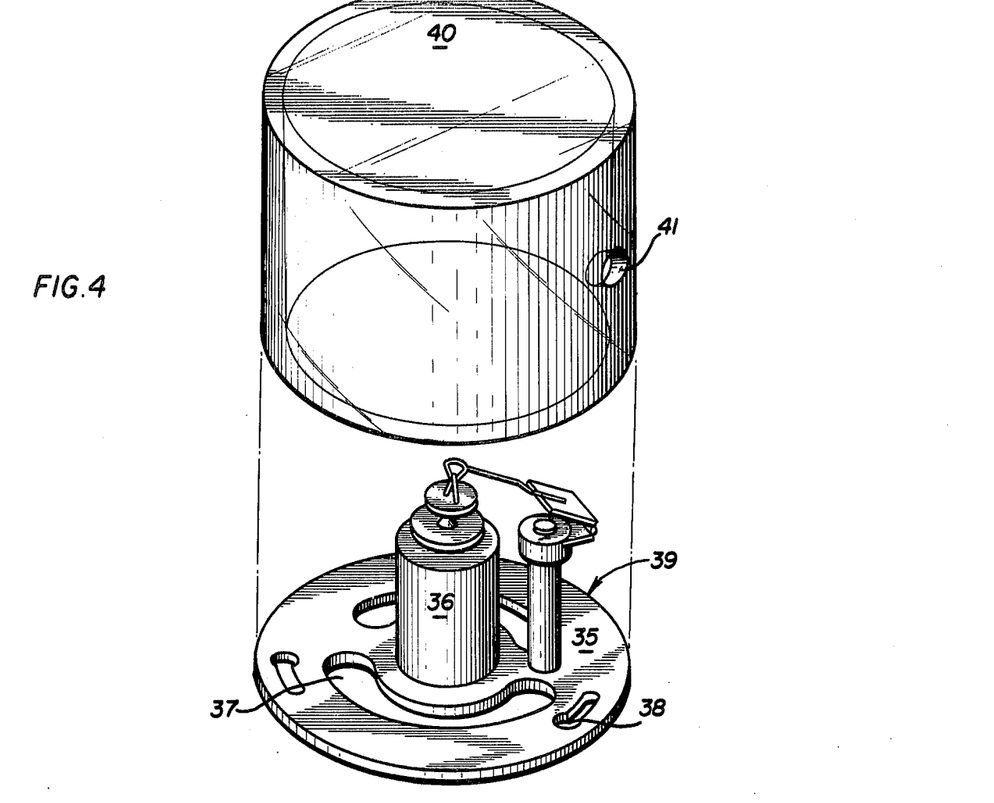
FIG. 4 illustrates transducer and calibration mechanisms of an upper housing constructed according to the invention.

FIG. 4 illustrates the components of electromechanical sensing device housing 15 in detail. Housing 15 consists of a slotted base plate 35 upon which a linear variable differential transformer 36 is centrally mounted. Openings 37 are provided for substantially open communication with lower housing 11. Slots 38 are provided for mounting of housing 15 on lower housing 11 by means of mounting posts (not shown) provided on lower housing cover 30. Also mounted on plate 35 is apparatus (generally 39) for calibration of transformer 36. Dome element 40 encloses the space above plate 35 and contains suitable ports (e.g., 41) for passage of electrical conduits.

The cooperative relationship of components of detector 10 is illustrated in detail in FIG. 2, which shows all parts of housing 11 assembled with housing 15 mounted in place. Housings 11 and 15 of detector apparatus 10 are so assembled and mounted with respect to each other as to provide gas-tight seals from the surrounding atmosphere. Gas flow into and out of detector 10 is respectively limited to inlet and outlet members. Armature 42 of transformer 36 extends through opening 32 of cover plate 30 and a disc-shaped platen 42a thereof contacts the surface of sheet 26.

Anesthesia system gas flow enters detector 10 through inlet 12 in housing 11. The flow is deflected by sidewall 22 of baffle 20 to assist in circulation about the space above and below elastic sheet 26 and to diminish the likelihood of vibration of the sheet by pressure changes. Mechanical deformation of the membrane (viz., variations in the vertical and/or horizontal dimensions) brought about by varying concentrations of anesthetic gas passing through the housing are detected by (and cause upward or downward movement of) armature 42 of transformer 36 which is biased into contact with the membrane. This mechanical movement of armature 42 is linearly translated into an electrical impulse (voltage output) which is carried to e.g., console 100, for translation into an informational signal. Because the short range deformation of sheet 26 follows anesthetic gas concentration in a linear manner, amplification of the transformer voltage output permits a direct reading of a voltage equal to percent concentration.

Figure 5:
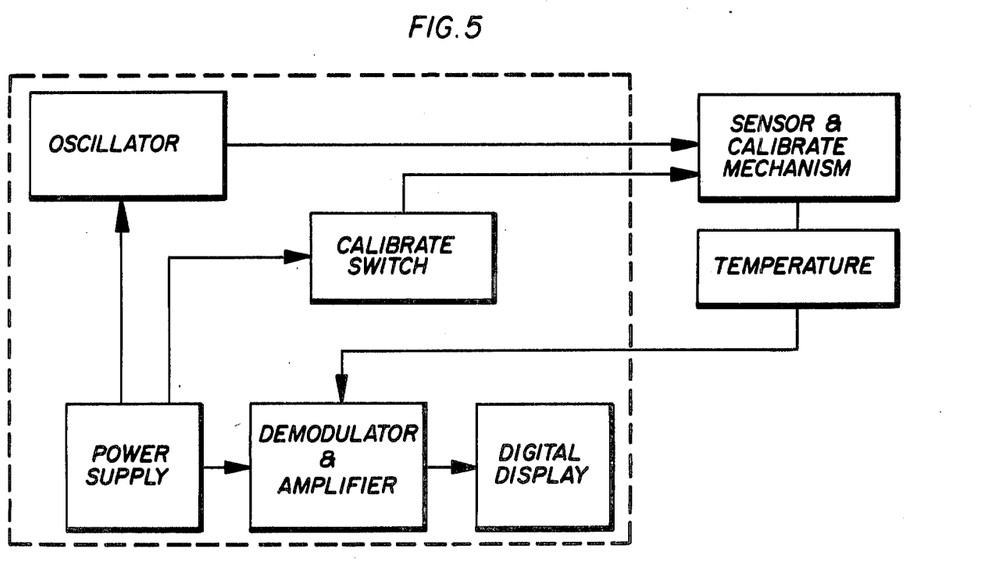
FIG. 5 is a block circuit diagram showing signal display apparatus in combination with detection apparatus of the invention.

FIG. 5 illustrates in simplified block circuit diagram form the interrelationship of electrical components typically involved in translating electrical impulses emanating from transformer 36 into a digital display.

FIG. 4 illustrates the function of preferred calibration (including temperature sensing and correcting) mechanisms. A suitable apparatus 39 for general calibration of the detector may simply comprise an electromagnetic mechanism 43 for selectively applying a weight 44 to the upper portion of armature 42. Calibration of the detector apparatus is achieved by adding a known weight to the armature such that the deformation of the diaphragm due to the weight is equal to the deformation due to a known concentration of anesthetic gas. This system facilitates calibration with no gas flow.

Information concerning variations in the temperature of gaseous flow may be derived from a thermistor device 45 mounted on base 35 to extend into lower housing 11 in a space adjacent diaphragm 26 (see FIG. 2). Information so derived may be automatically translated into a modification of the digital display according to a predetermined program.

Operation of detector apparatus of the invention may be more clearly understood upon consideration of the following commentary and illustrative examples.

In practice, the detector is affixed to an ordinary $CO_2$ absorber by means of standard sized anesthesia connectors on either the inspiratory or expiratory side of the anesthesia system circle. The patient tubing to or from mask or endotracheal tube is then attached to the other side of the detector. All connections are preferably sliding (push) fit. Care should be taken to assure that the detector is as nearly level as possible. While the instrument can operate well at angles up to 20° between the plane of the diaphragm and horizontal, it is desirable to take care in leveling.

Figure 6:
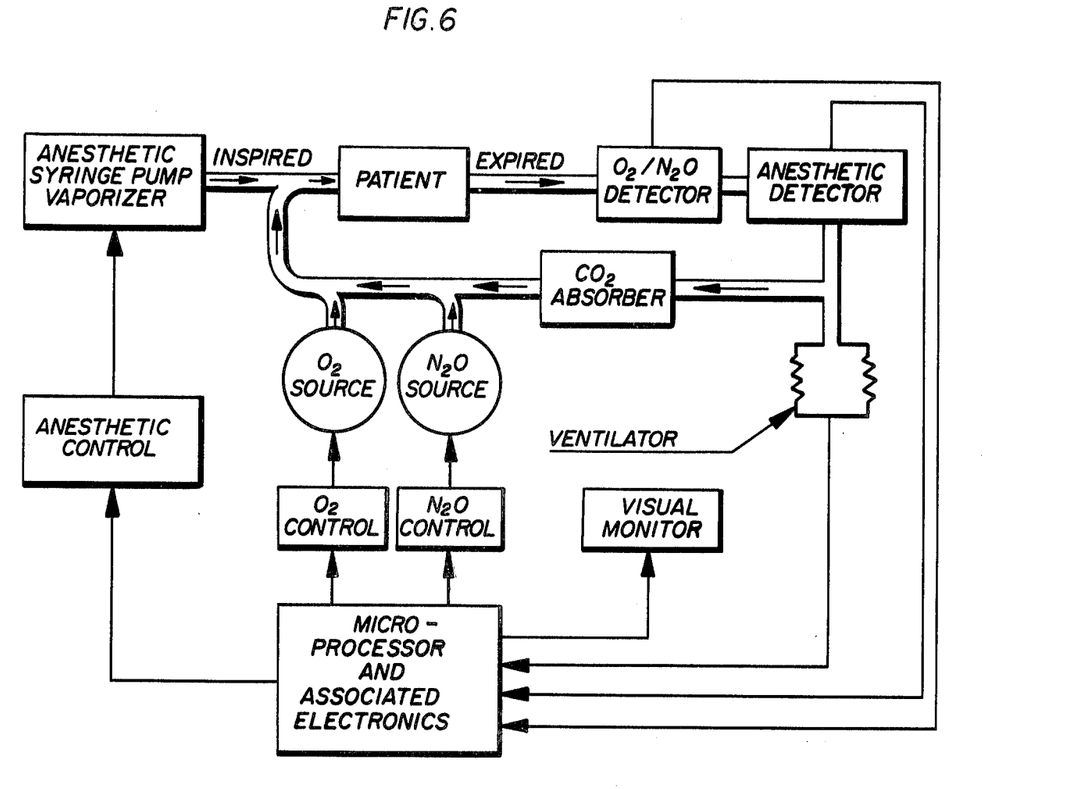
FIG. 6 is a block diagram of a closed loop anesthesia system incorporating the anesthetic detector of the invention as part of a fully automated control system.

Once the anesthesia circle is fully connected and the unit turned on, the following procedure may be followed prior to starting gaseous flow from the anesthesia generating machine (See, e.g., FIGS. 1 and 6).

(1) By means of a zero-set control, the digital panel meter 101 is adjusted to read 0.00.

(2) A "calibrate" actuator is depressed and held down while a variable "calibrate control" is adjusted so that the digital meter reads the number indicated on the calibration chart supplied with the instrument for the particular gas to be administered. For exemplary purposes only, if the gas is halothane, with the calibration weight in place, the digital display is set to read 2.00. If ethrane is the anesthesia being used, the scale would be set to read 1.2. If penthrane is the agent of choice, calibration should be adjusted to read 0.7. The calibration chart also would contain information regarding changes in the output reading due to varying concentrations of nitrous-oxide in the gas mixture. The portion of the total due to nitrous-oxide is ordinarily very small.

(3) Upon releasing the calibrate actuator, the digital display should return to 0.00. The anesthesia machine may now be turned on to deliver gas in the predetermined proportions as set by the physician. The digital display will indicate the gas concentration directly in percent. While most physicians prefer anesthesia measurements in terms of percent concentration in the gas mixture the monitor may be calibrated to read in minimum alveolar concentration (MAC) units if desired.

EXAMPLES 1-15

Anesthetic gas monitoring apparatus of the present invention was employed clinically in the course of fifteen surgical procedures described below.

A. Anesthesia Machines Used

Ohio Model 2000 and 3000 anesthesia machines equipped with two vernitol vaporizers were used for the majority of the cases. A Harris Lake Boyles machine modified with Ohio Vernitol side arm vaporizer was also used. When the Vernitol was equipped with a thermometer, the concentration of anesthetic was temperature corrected during the calibration procedures. When no thermometer was available, the following assumptions were made:

(a) Halothane - 100 cc. $O_2$ through the vaporizer produced 50 cc. of Halothane vapor; and (b) Ethrane - 100 cc. $O_2$ through the vaporizer produced 30 cc. of Ethrane vapor.

Temperature was then assumed to remain constant. This is the usual working procedure in clinical practice. Variations due to temperature are measurable but are of little clinical significance because of the efficiency of the vaporizers and lack of variation in operating room temperature.

B. Delivery System

All machines were equipped with jumbo soda lime circle absorber systems. Ohio disposable tubing with a bacterial filter was used on all cases with the exception of one pediatric case. In this case a "T" piece arrangement was used wherein the mixed expired gas was monitored after it left the anesthesia bag.

C. Calibration (1) Halothane

A 5 liter flow of $O_2$ was run through the detector and the meter was adjusted with the zero control to read zero. If the temperature of the vaporizer was available, the flow through anesthesia generator to give 3% Halothane in 5 L/min. flow was calculated. This was set on the generator and run through the detector. When the reading became stable, the meter was then set by adjusting the gain control to a reading of 3%. When temperature was not available, it was assumed that 300 cc. through the vaporizer and a 5 L/min. flow was equal to three percent.

When the above-described mechanical calibration apparatus was employed an additional step was added. After adjusting the zero and 3% points as described above, a 5 L/min. flow was run through the device until it returned to zero. The weight was then dropped and the meter reading was noted. This established a mechanical calibration number for this particular anesthetic agent.

(2) Ethrane

The procedure was the same as that used for halothane with the following exceptions:

(a) a total flow of either 3 L/min. or 6 L/min. was used;

(b) when no vaporizer temperature was available, it was assumed that 100 cc. through the vaporizer produced 30 cc. of ethrane vapor; and (c) calibration points used were zero and 3%.

D. Effects of Nitrous Oxide

When nitrous oxide was used, one of the following procedures was used. The calibration was performed with the nitrous oxide/oxygen mixture to be used during the case thus nulling the effect of nitrous oxide. The second alternative was to run the nitrous oxide mixture through the device after calibration with oxygen. The reading on the device could be set as a negative number after going back to the original oxygen zero.

With the gain used for halothane, nitrous oxide 50% to 70% introduces an increase in the meter reading of between 0.2 to 0.4%. When ethrane is used, this factor is proportionately higher because ethrane causes less deflection of the membrane requiring a higher electrical gain. Typical nitrous oxide readings for 66% $N_2O$ are 0.5 to 0.6%.

E. Results

Table I below sets out various pertinent facts relating to the fifteen surgical procedures performed. During Case No. 5, the reading generated by the monitoring apparatus unexplainably showed a slow gradual increase over the first two hours and indicated a substantially higher halothane concentration than appeared to be delivered by the generator. In all other test cases, accuracy and reproducibility exceeded measurement capabilities of the anesthesia generators and devices (such as those of U.S. Pat. Nos. 3,498,309 and 3,536,088) employed for comparison.

TABLE I

| CASE NO. | OPERATION | AGE | WT. (Kg.) | SEX | ANES-THETIC | SYSTEM | MONITOR LOCATION | TEST DURATION (Hours) | RESPIRATION | AIR WAY |
|---|---|---|---|---|---|---|---|---|---|---|
| 1 | D & C, Sigmoidoscopy | 60 | 68 | F | $N_2O$ - Narcotic | Semi-closed Absorber System (SCA) | Expire | 1 | Spontaneous | Mask |
| 2 | Colon Resection | 67 | 85 | F | Halothane - $N_2O$ | Closed Circuit SCA | Inspire | 2 | Mechanical Ventilation | Tube |
| 3 | Amputation - Gangrenous Finger | 53 | 65 | M | Halothane - $N_2O$ | SCA | Inspire | 1 | Spontaneous | Mask |
| 4 | Skin Graft, Right Leg Melanoma | 54 | 82 | F | Halothane - $O_2$ | Closed Circuit | Inspire | 1.5 | Spontaneous | Tube |
| 5 | Ligation Patent Ductus | 11 | 19.7 | F | Halothane - $N_2O$ | SCA | Expire | 4 | Hand Ventilation | Tube |
| 6 | Correction of Coarctation of the Aorta | 1 | 4.5 | M | Halothane - $N_2O$ | "T" Piece | Expire | 4 | Hand Ventilation | Tube |
| 7 | Open Lung Biopsy | 38 | 65 | F | Ethrane | SCA | Inspire | 2 | Hand Ventilation | Tube |
| 8 | Repair of Wound Dehiscence Post Enucleation, Right Eye | 50 | 110 | M | Halothane - $N_2O$ | SCA | Expire | 2 | Spontaneous | Tube |
| 9 | Craniotomy, Evacuation Cerebral | 48 | 60 | M | Halothane - $N_2O$ | SCA | Expire | 3.5 | Mechanical Ventilation | Tube |

TABLE I-continued

| CASE NO. | OPERATION | AGE | WT. (Kg.) | SEX | ANES-THETIC | SYSTEM | MONITOR LOCATION | TEST DURATION (Hours) | RESPIR-ATION | AIR WAY |
|---|---|---|---|---|---|---|---|---|---|---|
| 10 | Hematoma Blaylock Shunt (Tetrology of Fallot) | 2 | 8.5 | F | Halothane - $N_2O$ | SCA | Inspire | 5.5 | Hand Ventilation | Tube |
| 11 | Closed Reduction Fracture, Right Wrist | 6 | 30 | M | Halothane - $N_2O$ | SCA | Inspire | 1.5 | Spontaneous | Tube |
| 12 | Repair Extensor Tendons, Right Hand | 21 | 61 | M | Ethrane - $N_2O$ | SCA | Expire | 1.5 | Spontaneous | Mask |
| 13 | Exploratory Lap Hysterectomy | 34 | 81 | F | Ethrane | Closed Circuit | Inspire | 3.5 | Hand Ventilation | Tube |
| 14 | Cholecystectomy | 42 | 74 | F | Ethrane - $N_2O$ | SCA | Inspire | 2.5 | Mechanical Ventilation | Tube |
| 15 | Splenectomy Hodgkins Staging | 29 | 100 | M | Ethrane - $N_2O$ | SCA | Inspire | 4 | Mechanical Ventilation | Tube |

In the course of further developmental testing of devices of the invention, a comparison was made with a standard commercial infrared halothane analyzer. A monitor of the invention and the infrared analyzer were "run" in series after calibration of the instruments with standardized quantities of halothane (standards of 1.60% and 3.00% halothane in oxygen) and tested in surgical procedures as follows.

Both the monitor and infrared device were adjusted to read 3% using the standard and attached in series to an Ohio Anesthesia Machine. Because the infrared analyzer draws 2 liters/minute for measurement, it was connected behind the monitor cartridge. The infrared analyzer measurements were very fast, with sample-to-read times on the order of two seconds. The monitor tended to integrate minute variations and yet indicate changes (except for zero to full scale) in times on the order of six seconds. Halothane concentrations were varied throughout the surgical procedure and, at several points throughout the test, both standards of 1.60 and 3.00% halothane were introduced to check the calibration. It was found that the infrared analyzer required re-calibration about every fifteen minutes while the monitor of the invention required no adjustment for gain or zero at any time after start-up. Plus or minus 0.1% or better sensitivity to alvealor concentration of halothane was achieved in all tests of the monitor of the invention; with adverse effects of moisture virtually eliminated by use of the bacteria/moisture screen. No substantial thermal variations in accuracy were noted.

It is proposed that the faster, more linear, and more readily reproducible response to anesthetic gas concentration obtained by devices of the invention is attributable, at least in part, to their greater sensitivity to all dimensional changes (including horizontal, vertical, and composite vectors) across the entire elastic membrane employed, rather than, for example, mere one-dimensional length changes. Put another way, by measuring deformation rather than length changes under tension, the devices of the invention are believed to be substantially more sensitive to all dimensional aspects of the swelling phenomenon than those of the prior art. It is therefore expected that equally satisfactory results may be obtained through use of membranes in shapes other than that of a disc which are attached at their periphery to relatively rigid or thickened members having other than a hoop shape.

The numerous advantages attending use of devices of the invention indicate its exceptional suitability for use in a wholly automatic closed loop anesthesia system such as illustrated in FIG. 6 wherein a single visual monitor might display such factors as tidal volume, minute volume, respiratory rate, calculated cardiac output, derived cardiac output, expired oxygen concentration, expired anesthetic concentration, quantity of anesthesia delivered and the like. In such a system, information concerning anesthetic gas concentration may provide a basis for programming the input and exhausting of all gases (oxygen, nitrous oxide, etc.) administered to the patient throughout a surgical procedure.

Further benefits to be obtained through use of the monitor of the invention include:

1. Enhanced potential for use of reduced gas flow rates. Levels of 5 liters per minute (oxygen or oxygen with nitrous oxide and anesthesia) are now standard. Levels of 2 liters per minute or less would appear to be possible because of greater control capabilities donated by the monitor. This would substantially lower the total cost of surgical procedures and diminish potential operating room pollution.

2. Greater feasibility for expanded use of closed loop systems. With greater accuracy in quantitative detection of anesthetic gas and potentially lower flow rates, exhaust-free closed loop systems became more practical. Carbon dioxide can be easily absorbed and anesthetic and other gases added only when needed.

3. Greater sensitivity to the patient's dynamic physiological state. The constant monitoring capacity provided by the invention can generate valuable indications of changes in patient cardiac output and leaks in the anesthesia circuit. If, for example, there is no change in gas input and a decrease in the patient level is observed, there may be a leak in the administration circuit. If no such leak is found, then changes in uptake are probably due to decreased cardiac output and stimulant administration or other action by the anesthesiologist may be required.

4. Enhanced potential for continuous record keeping and fully automatic anesthesia delivery. The monitor of the invention provides a BCD output which may be utilized for continuous record keeping in keeping with ECG, blood pressure and the like. This signal, in combination with that of an oxygen analyzer of standard construction, may be used to provide for computerized automatic anesthesia delivery as illustrated in FIG. 6.

Numerous modifications and variations of the invention are expected to occur to those skilled in the art upon consideration of the foregoing disclosure. Therefore, only such limitations as appear in the appended claims should be placed thereon.

What is claimed is:

1. An improvement in electromechanical devices for detection and quantification of an anesthetic gas in gaseous flow in an anesthesia administration system wherein presence of said anesthetic gas is detected and quantified as a function of proportional reversible swelling of an anesthetic gas, said improvement comprising:
   a first housing having an inlet and outlet for gaseous flow therethrough;
   a membrane of anesthetic gas-sensitive elastic material;
   means for substantially horizontally mounting said membrane in said first housing and for substantially supporting said membrane along its entire periphery;
   a second housing including electromechanical means for (a) quantitatively detecting mechanical deformation of said membrane in said first housing resulting from reversible swelling in response to the concentration of anesthetic gas in gaseous flow therethrough, and (b) translating detected deformation of said membrane into an electrical signal; and
   means mounting said first and second housings in sealed relation with substantially open communication therebetween for gaseous flow.

2. The improvement of claim 1 wherein said membrane is a silicone rubber membrane.

3. The improvement of claim 2 wherein said silicone rubber membrane is disc-shaped and said mounting means includes a rigid ring affixed to the periphery of said membrane.

4. The improvement of claim 1 wherein said electromechanical detecting means comprises linear variable differential transformer means.

5. The improvement of claim 4 further including means for calibration of said transformer means to provide a predetermined signal for a fixed concentration of anesthetic gas in said gaseous flow.

6. The improvement of claim 5 further including means for calibration of said transformer means in response to changes in gaseous flow temperature.

7. The improvement of claim 1 further including water vapor condensing, bacterial screening means in said first housing for restricting passage of water vapor and bacteria from said first housing to said second housing.

8. The improvement of claim 1 further including baffling means in said first housing for modulating pressure changes in gaseous flow therethrough.

9. The improvement of claim 1 further including means for varying the quantity of a gas entering gaseous flow in response to the detected deformation of said membrane.

10. A closed loop anesthesia administration system comprising:
    a closed loop conduit for gaseous flow to and from a patient;
    a source of anesthetic gas and means for delivery of known quantities of said gas to said conduit;
    a source of oxygen and means for delivery of known quantities of oxygen to said conduit;
    means for quantitative detection of anesthetic gas in said conduit and comprising,
    a first housing having an inlet and outlet for gaseous flow therethrough,
    a membrane of anesthetic gas sensitive elastic material,
    means for substantially horizontally and vertically mounting said membrane in said first housing and for substantially supporting said membrane along its entire periphery,
    a second housing including electromechanical means for (a) quantitatively detecting mechanical deformation of said membrane in said first housing resulting from reversible swelling in response to the concentration of anesthetic gas in gaseous flow therethrough, and (b) translating detected deformation of said membrane into an electrical signal, and
    means mounting said first and second housings in sealed relation with substantially open communication therebetween for gaseous flow,
    means co-active with said detection means and said delivery means for varying the quantities of oxygen and anesthetic gas to said conduit in response to detected changes in the quantity of anesthetic gas in said conduit.

11. An improvement in electromechanical devices for detection and quantification of an anesthetic gas in gaseous flow in an anesthesia administration system wherein presence of said anesthetic gas is detected and quantified as a function of proportional reversible swelling of an elastic material in contact with varying amounts of the anesthetic gas, said improvement comprising:
    a first housing having an inlet and outlet for gaseous flow therethrough;
    a membrane of anesthetic gas-sensitive silicone rubber;
    means for substantially horizontally mounting said membrane in said first housing and for substantially supporting said membrane along its entire periphery;
    a second housing including linear variable differential transformer means for (a) quantitatively detecting mechanical deformation of said membrane in said first housing resulting from reversible swelling in response to the concentration of anesthetic gas in gaseous flow therethrough, and (b) translating detected deformation of said membrane into an electrical signal; and
    means mounting said first and second housings in sealed relation with substantially open communication therebetween for gaseous flow.

* * * * *